(12) United States Patent
Dean et al.

(10) Patent No.: US 6,524,314 B1
(45) Date of Patent: Feb. 25, 2003

(54) INTERLOCKING INTRAMEDULLARY NAIL

(76) Inventors: John C. Dean, 4805 Island Dr., Midland, TX (US) 79707; Dennis C. Moad, 906 San Jacino St., Lockhart, TX (US) 78644

( * ) Notice: Subject to any disclaimer, the term of this patent is extended or adjusted under 35 U.S.C. 154(b) by 0 days.

(21) Appl. No.: 09/935,526

(22) Filed: Aug. 24, 2001

(51) Int. Cl.⁷ .............................................. A61B 17/56
(52) U.S. Cl. ...................................................... 606/64
(58) Field of Search ............................. 606/62, 63, 64, 606/67, 65

(56) References Cited

U.S. PATENT DOCUMENTS

| 4,644,943 A | 2/1987 | Thompson et al. |
| 4,817,591 A | 4/1989 | Klaue |
| 4,858,601 A | 8/1989 | Glisson |
| 4,913,137 A | 4/1990 | Azer et al. |
| 5,531,748 A | 7/1996 | de la Caffiniere |
| 5,779,705 A | 7/1998 | Matthews |
| 6,010,505 A | 1/2000 | Asche et al. |
| 6,019,761 A | 2/2000 | Gustilo |
| 6,022,352 A | 2/2000 | Vandewalle |
| 6,443,954 B1 * | 9/2002 | Bramlet et al. ............... 606/62 |

* cited by examiner

Primary Examiner—Eduardo C. Robert
(74) Attorney, Agent, or Firm—Bacon & Thomas, PLLC

(57) ABSTRACT

An interlocking intramedullary nail assembly including an intramedullary nail, a first lag screw, a second lag screw and a locking screw. The first and the second lag screws are arranged to mate with one another and are received by the intramedullary nail at opposite ends of a transverse through bore passing through a distal portion of the nail. The interlocking screw is used to operatively couple the first lag screw and second lag so as to fix the first and the second lag screws to the nail.

11 Claims, 10 Drawing Sheets

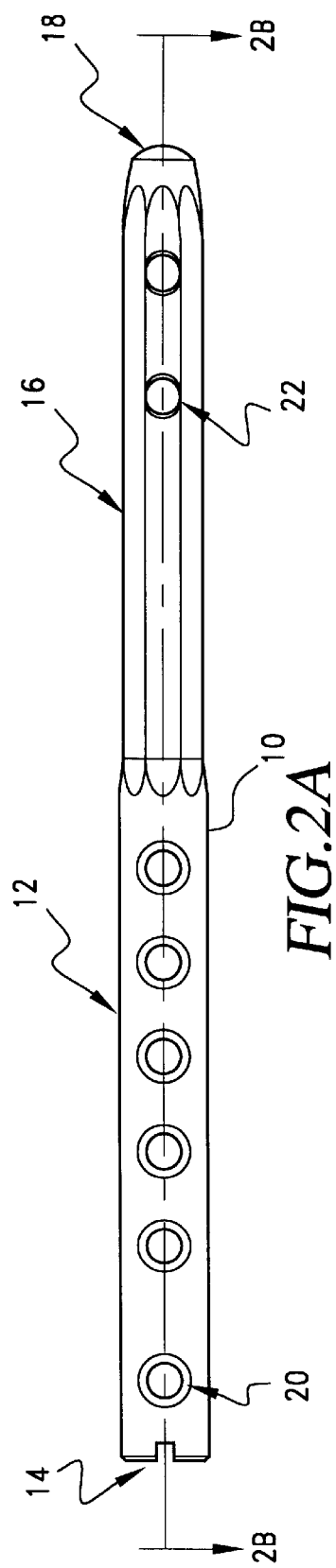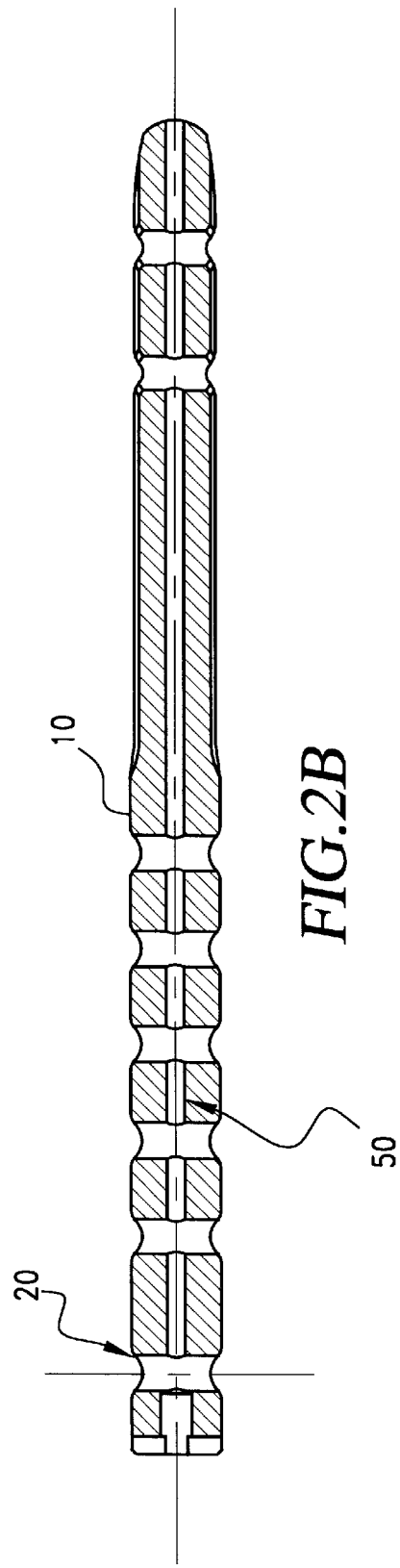

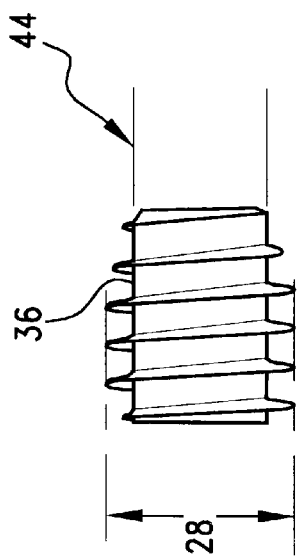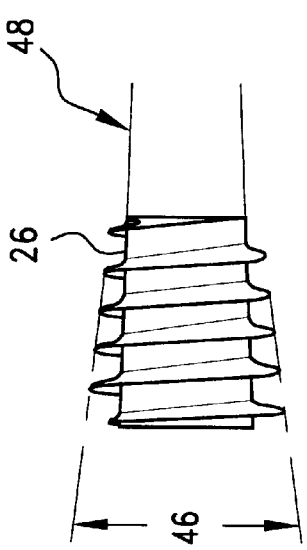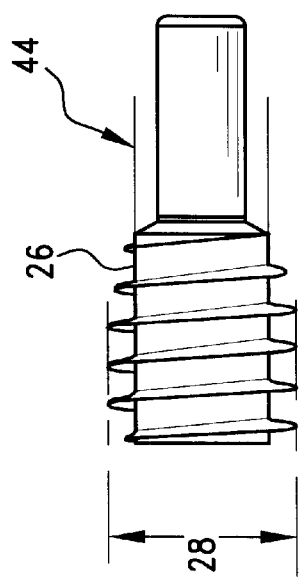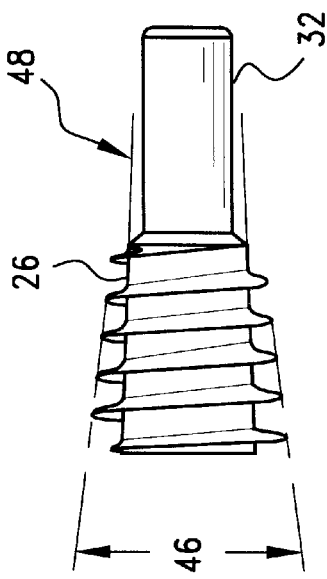

INTERLOCKING INTRAMEDULLARY NAIL

BACKGROUND OF THE INVENTION

1. Field of the Invention

The present invention relates to an improved intramedullary nail and method for stabilizing fractures of the femur. More specifically, the present invention relates to a surgical interlocking intramedullary nail including an interlocking screw assembly for immobilization of distal femur parts involved in fractures occurring in the condylar and supracondylar portions of the femur.

2. Description of the Prior Art

It is known that bone parts or fragments involved in fractures of the femur are difficult to stabilize satisfactorily. Since the femur functions as a weight bearing bone, the femoral fractures often take longer to heal and there is potential for greater complications in setting the fracture than in non-weight bearing bones. Furthermore, it is well understood that patients that remain inactive following surgery have an increase in the risk of serious complications including the development of blood clots and pneumonia. Therefore after stabilizing a femoral fracture, early mobilization of a patient is necessary so that the femur will heal quickly, with stronger repair and less likelihood of complications.

In treating a femoral fracture, it is standard practice to use a fixation device adapted to facilitate recovery of the fractured bone. The fixation device provides immobilization of the bone fragments and stabilization of the fractured femur, thus providing earlier mobilization and weight bearing of a patient. The fixation device is attached to or inserted into the femur and cooperates with the bone fragments and the femoral shaft to stabilize the bone. As the bone heals, the fixation device allows the bone fragments to compress into each other so the fragments grow together to restore the bone.

Two prevalent types of femoral fractures are supracondylar or "T-type" condylar fractures about the distal femur. A number of different fixation devices, both external and implantable, have been devised for fixation of supracondylar and condylar fractures. In the past, treatment of condylar or supracondylar fractures consisted of stabilizing the bone portions with plates and screws. However, in using plates and screws, invasive surgery is required and includes considerable dissection of the thigh in order to expose the fracture so as to attach the plates and screws. The resultant devasculariztion of the distal portion of the femur has lead to a high frequency of complications of delayed union of the bone sections, osseous fracture and infection. Additionally, due to the muscular stresses in the region of the condylus and supracondylus, the treatment may involve undesirable post-operative procedures and complications including the bending or breaking of the plates, loosening of the screws and migration of the femoral shaft.

Recently, intramedullary (IM) nailing has become a standard procedure for treating supracondylar and condylar fractures. In its basic form, IM nailing consists of driving a rod-like nail into the intramedullary bone canal of the femur to stabilize transverse fractures of the femur. However, such IM nails often fall short to provide effective fixation or immobilization for supracondylar and condylar fractures since they fail to sufficiently compress bone fragments. Improvements have been made on IM nails to further stabilize the bone fragments by introducing interlocking cross-bolts or screws through the nail that are fixed on both sides of the fracture.

Despite their advantages over plate and screw fixation devices, there are still complications that arise with interlocking IM nails. One difficulty is that the screws may loosen, creating a decrease in screw fixation which results in screw toggling, or in a worst case scenario, complete screwing out of the nail. Another difficulty results from the oblique position of the condyles with respect to the shaft of the femur. Since the fixation of the screws is often transverse to the femoral shaft, the screws do not extend through the major mass of the cancellous bone of each condylus. Furthermore, the sizes of many current screws used with the IM nails do not achieve sufficient purchase in the bone. Stabilizing the fracture is further compounded by the fact that the bone is often of poorer quality.

Known IM nails have been designed for treatment of condylar and supracondylar fractures. For example, U.S. Pat. No. 5,779,705 issued to Matthews and U.S. Pat. No. 6,010,505 Asche et al., which are herein incorporated by reference in their entirety, each disclose an intramedullary device having an IM nail and interlocking bolts or screws to grip and stabilize the femoral condyles with respect to the femoral shaft. The disclosures of the references are considered to establish the state art for condylus and supracondylus IM nails. Each of the devices disclosed thereby addresses the desirability of compression in the treatment of femoral fractures and emphasizes compression of the condyles with respect to the femoral shaft.

Matthews discloses an intramedullary nail incorporating a Cruciate arrangement of two obliquely crossing locking bolts such that each condyle of the femur is gripped by an individual bolt. The Cruciate or staggered/crossed configuration of holes permits two distal locking bolts to be inserted.

Asche et al. discloses a supracondylar bone nail that has an elongated shank with two bends. The first bend begins at a distance from the distal end of about a quarter or a third of the length of the nail at an angle of about 8°. The second bend begins in the last third of the nail length if looking from the distal end and has an angle of approximately 3°. The nail includes transverse bores in the distal and proximal end which are adapted to accommodate screws.

Although effective results have been achieved with the above noted IM nails, problems of internal fixation still persist. Therefore, it is desirable to modify an IM nail so as to achieve greater internal fixation of the condyles and mitigate screw loosening and toggling.

SUMMARY OF THE INVENTION

To meet the above noted desires, it is an object of the present invention to provide an interlocking intramedullary nail for fixation of the distal femur which overcomes certain disadvantages of the prior art devices while maintaining their advantages. The present invention provides an interlocking intramedullary nail that aims to achieve greater fixation and immobilization of condylus and supracondylus fractures of the femur.

According to one embodiment of the present invention, the interlocking intramedullary nail comprises an intramedullary nail, a first lag screw, a second lag screw and a locking screw, all being adapted to accommodate one another. The nail is configured to be inserted from a distal end of the femur below the condylus and has a distal end with a transverse bore extending therethrough. The first lag screw has a distal end with a cylindrical first portion and an axial through hole. The first lag screw is arranged to be inserted into one end of the transverse bore. The second lag screw has an axial through hole and is adapted to receive the cylindrical portion of the first lag screw at another end of the transverse bore. The locking screw is adapted to be inserted into the axial through hole of the second lag screw so as to thread onto the first lag screw and the second lag screw.

According to a second embodiment, the interlocking intramedullary nail has at least one transverse distal bore that is angled with respect to a longitudinal axis of the nail such that the first and second lag screws extend obliquely from the intramedullary nail.

According to another variant of the invention, the first lag screw and the second lag screw each may include a major external thread diameter having a taper. Further, according to yet another variant of the invention, the first lag screw and the second lag screw each may include a minor external thread having a taper. Still further, according to another embodiment of the invention, the first lag screw and the second lag screw each may include a major external thread diameter having a taper and a minor external thread diameter having a taper.

For a better understanding of the present invention, together with other and further objects thereof, reference is made to the following description, taken in conjunction with the accompanying drawings describing the preferred embodiments thereof.

BRIEF DESCRIPTION OF THE DRAWINGS

FIG. 2A is a side view of an embodiment of the intramedullary rod according to the present invention;

FIG. 2B is a cross-sectional view of the embodiment of the intramedullary rod of FIG. 2A;

FIG. 6 is a side view of a second embodiment of a first lag screw according to the present invention;

FIG. 7 is a side view of a second embodiment of a second lag screw according to the present invention;

FIG. 8 is a side view of a third embodiment of a first lag screw according to the present invention;

FIG. 9 is a side view of a third embodiment of a second lag screw according to the present invention;

DETAILED DESCRIPTION OF THE PREFERRED EMBODIMENTS

Figure 1:
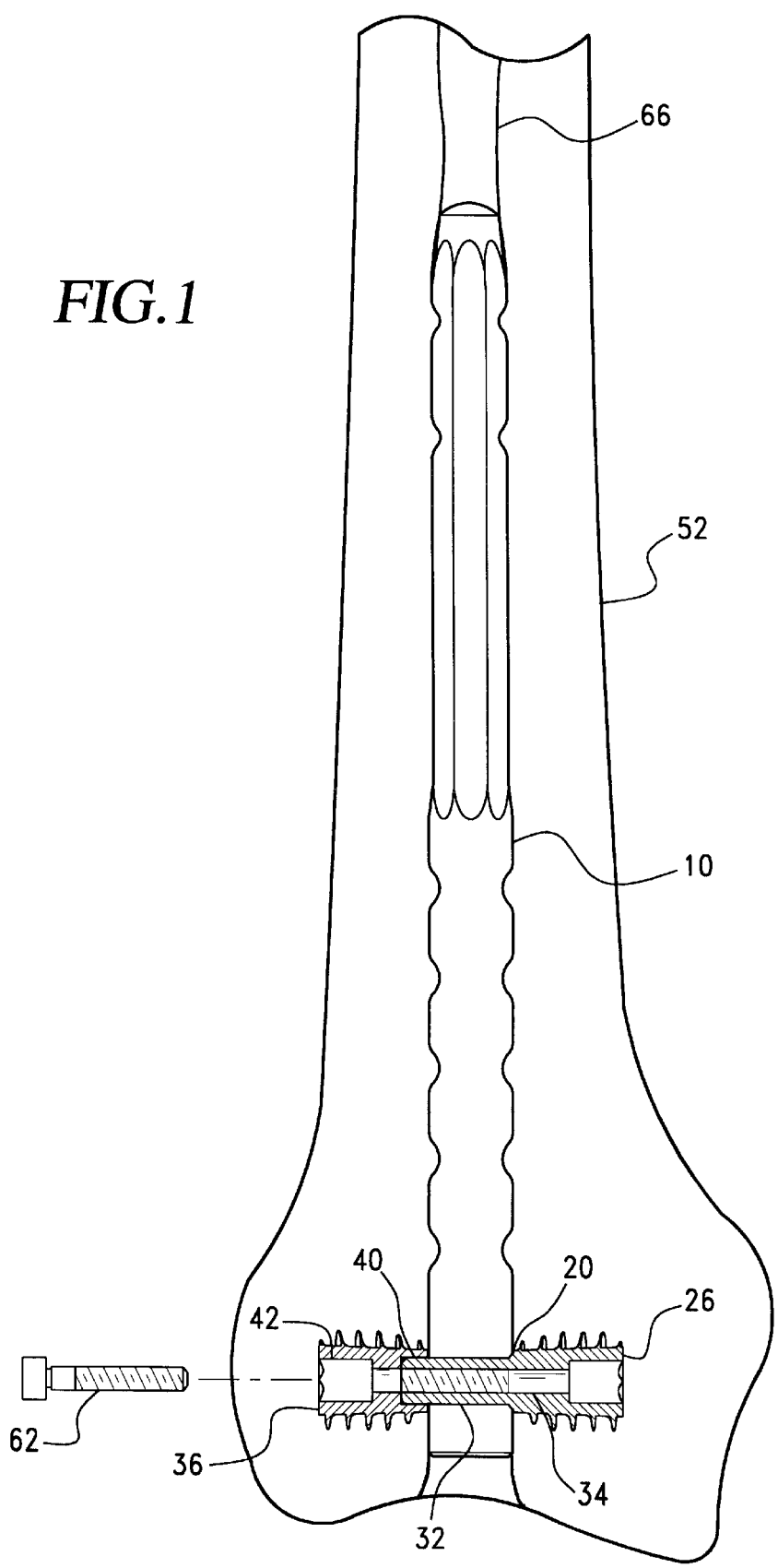
FIG. 1 shows an elevation cutaway view of an intramedullary nail according to the present invention showing its location in a distal end of a femur.

As shown in FIG. 1 according to a preferred embodiment of the invention, the distal portion of a femur 52 is shown which accommodates an intramedullary nail 10 with an elongate first lag screw 26 and a second lag screw 36. The first lag screw 26 and the second lag screw 36 receive a locking screw 62. The nail 10 is installed within the medullary or marrow canal 66 of the femur 52 in accordance with known medical procedures.

FIG. 2A is a side view of one embodiment of the nail 10. The basic structure of the nail 10 includes a distal portion 12 having a distal end 14 and a proximal portion 16 having a proximal end 18. The distal portion 12 has at least one transverse bore 20 and the proximal portion 16 has at least one transverse bore 22.

FIG. 2B shows a cross-sectional view of FIG. 2A. The transverse bore 20 is generally arranged at a 90° angle with respect to the longitudinal axis of the nail 10. The nail 10 is provided with an axial through hole 50 along its longitudinal axis.

Figure 3A:
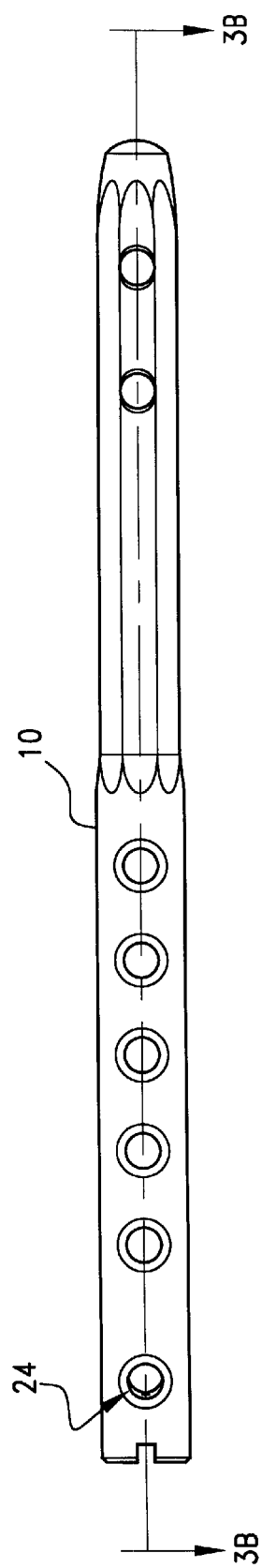
FIG. 3A is a side view of another embodiment of the intramedullary rod according to the present invention.
Figure 3B:
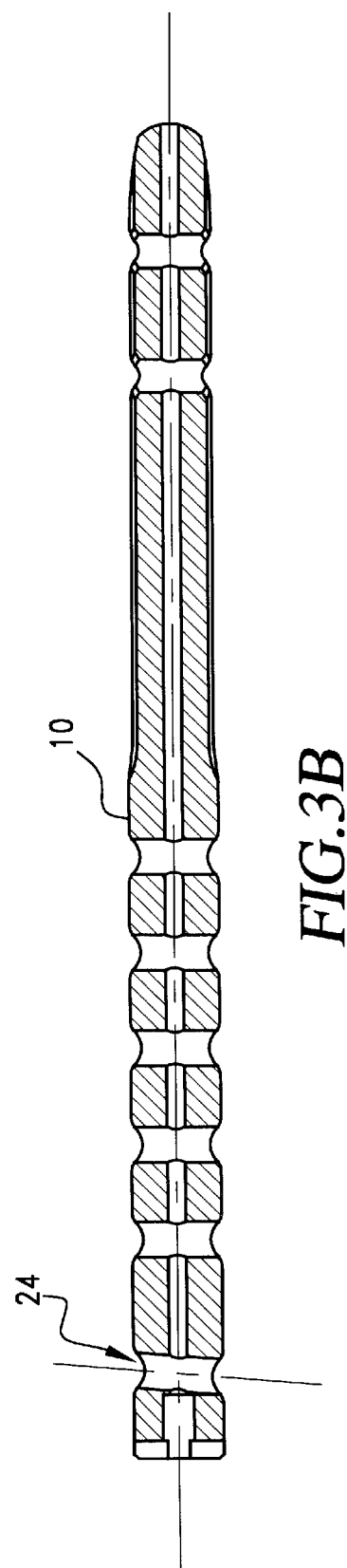
FIG. 3B is a cross-sectional view of the embodiment of the intramedullary rod of FIG. 3A.

FIGS. 3A and 3B show another embodiment of the nail 10 whereby a transverse bore 24 extends at an angle with respect to the longitudinal axis of the nail 10.

Figure 4A:
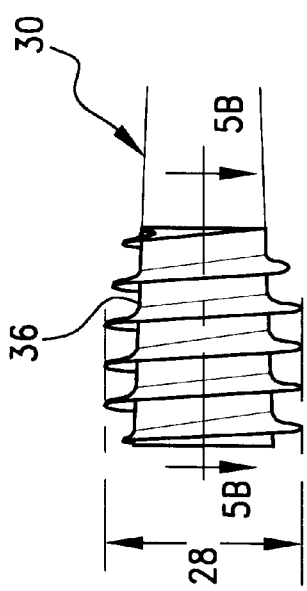
FIG. 4A is a side view of a first embodiment of a first lag screw according to the present invention.
Figure 4B:
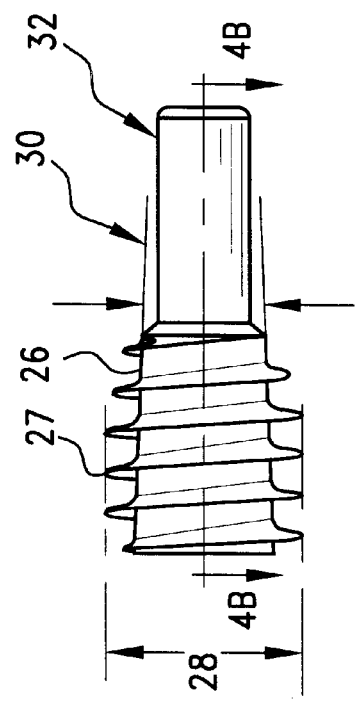
FIG. 4B is a cross-sectional view of the first embodiment of the first lag screw of FIG. 4A.

One preferred embodiment of the first lag screw of the invention is shown in FIGS. 4A and 4B. According to this embodiment, the first lag screw 26 divides into an outer threaded portion 27 at a first end and an outer cylindrical portion 32 at a second end. The outer threaded portion 27 and the outer cylindrical portion 32 are axially spaced along the length of the first lag screw 26. The outer threaded portion 27 has a constant outer diameter 28 and a minor diameter 30 located at the roots of the threads which progressively decreases from the first end to an end of the outer threaded portion 27 that is adjacent to the outer cylindrical portion 32. FIG. 4B shows a cross-sectional view of FIG. 4A along the plane D—D illustrating the internal configuration of the first lag screw 26. The first lag screw 26 internal configuration includes an axial bore 34 which includes a first threaded portion 70 extending axially from the second end a predetermined distance into the first lag screw 26.

Corresponding to the embodiment of the first lag screw 26 in FIGS. 4A and 4B, FIGS. 5A and 5B show a second lag screw 36 for mating with and receiving the first lag screw 26. Similar to the first lag screw 26 in FIGS. 4A and 4B, the threaded portion of the second lag screw 36 has a constant threaded outer diameter 28. The outer threaded portion also includes a minor diameter 30 located at the roots of the threads 30 and progressively decreases from a first end to a second end of the second lag screw 36.

Figure 5A:
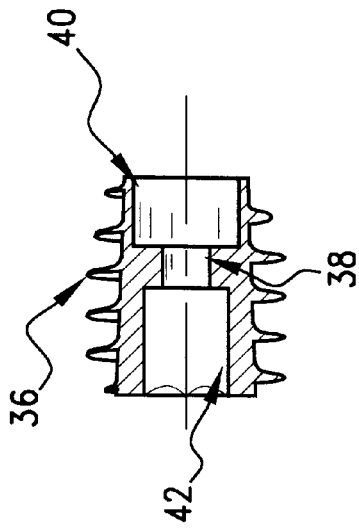
FIG. 5A is a side view of a first embodiment of a second lag screw according to the present invention.
Figure 5B:
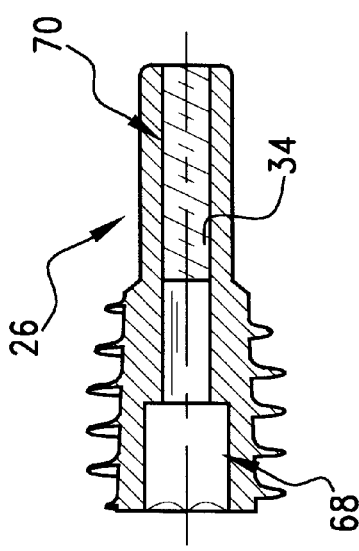
FIG. 5B is a cross-sectional view of the first embodiment of the second lag screw of FIG. 5A.

FIG. 5B shows a cross-sectional view of FIG. 5A along the plane E—E illustrating the internal configuration of the second lag screw 36. The internal configuration of the second lag screw 36 includes an axial through hole 38 having a screw seat 42 located at a first end and a mating portion 40 located at a second end. The screw seat 42 and the mating portion 40 are axially spaced along the length of the screw. The mating portion 40 is adapted to cooperate with the first outer cylindrical portion 32 of the first lag screw 26. The mating portion 40 includes a recess formed by the second lag screw 36 and extends into the second lag screw 36 a predetermined distance. The recess of the mating portion 40 is dimensioned to accommodate the first outer cylindrical portion 32 of the first lag screw 26. Moreover, the screw seat 42 acts as a stop for a locking screw as it is threaded onto the first lag screw 26 and the second lag screw 36. The screw seat 42 includes a recess formed by the second lag screw 36 and extends axially from the first end into the second lag screw 36 a predetermined distance.

FIGS. 6 and 7 each show another embodiment of both the first lag screw 26 and the second lag screw 36. Specifically, the threaded outer diameter 28 and the inner threaded diameter 44 each have diameters that remain constant. The internal configuration of the first lag screw 36 and the second lag screw 44 is the same as illustrated in FIGS. 4B and 5B respectively.

FIGS. 8 and 9 each show yet another embodiment of both the first lag screw 26 and the second lag screw 36. Specifically, in FIG. 8 the major external thread portion 46 of the first lag screw 26 progressively decreases from the first end to the end adjacent to the outer cylindrical portion 32. The minor diameter 48 at the roots of the threads of the first lag screw also progressively decreases from the first end to the end adjacent to the outer cylindrical portion 32. FIG. 9 shows that the major external thread portion 46 of the second lag screw 36 progressively decreases from the first end to the second end. Morever, the minor diameter 48 at the roots of the threads of the second lag screw 36 also progressively decreases from the first end to the second end.

Figure 10:
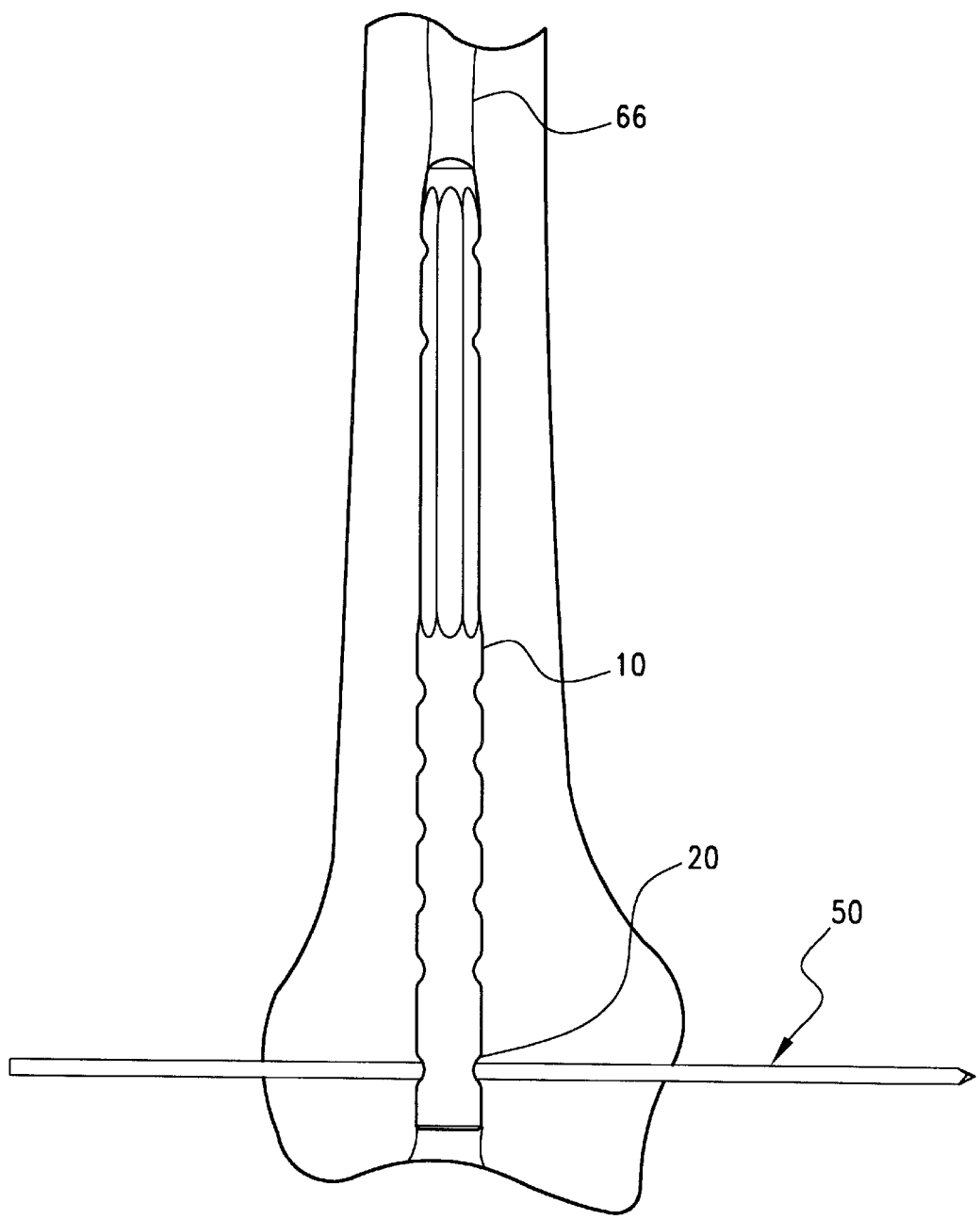
FIG. 10 is a plan view of an embodiment of the present invention showing the intramedullary nail installed in the distal portion of the femur along with a guiding lance.

Intramedullary nails in accordance with this invention are introduced into the femur through the knee. After exposing the femur, the nail is inserted through a bore which is in line with the axis of the intramedullary canal. FIG. 10 shows a nail 10 that has been inserted into the intramedullary canal 66. A pilot through hole is drilled through the femur along the axis of a distal transverse bore 20. In a preferred embodiment of the present invention, a guide wire 50 is passed through of the distal transverse bore 20.

Figure 11:
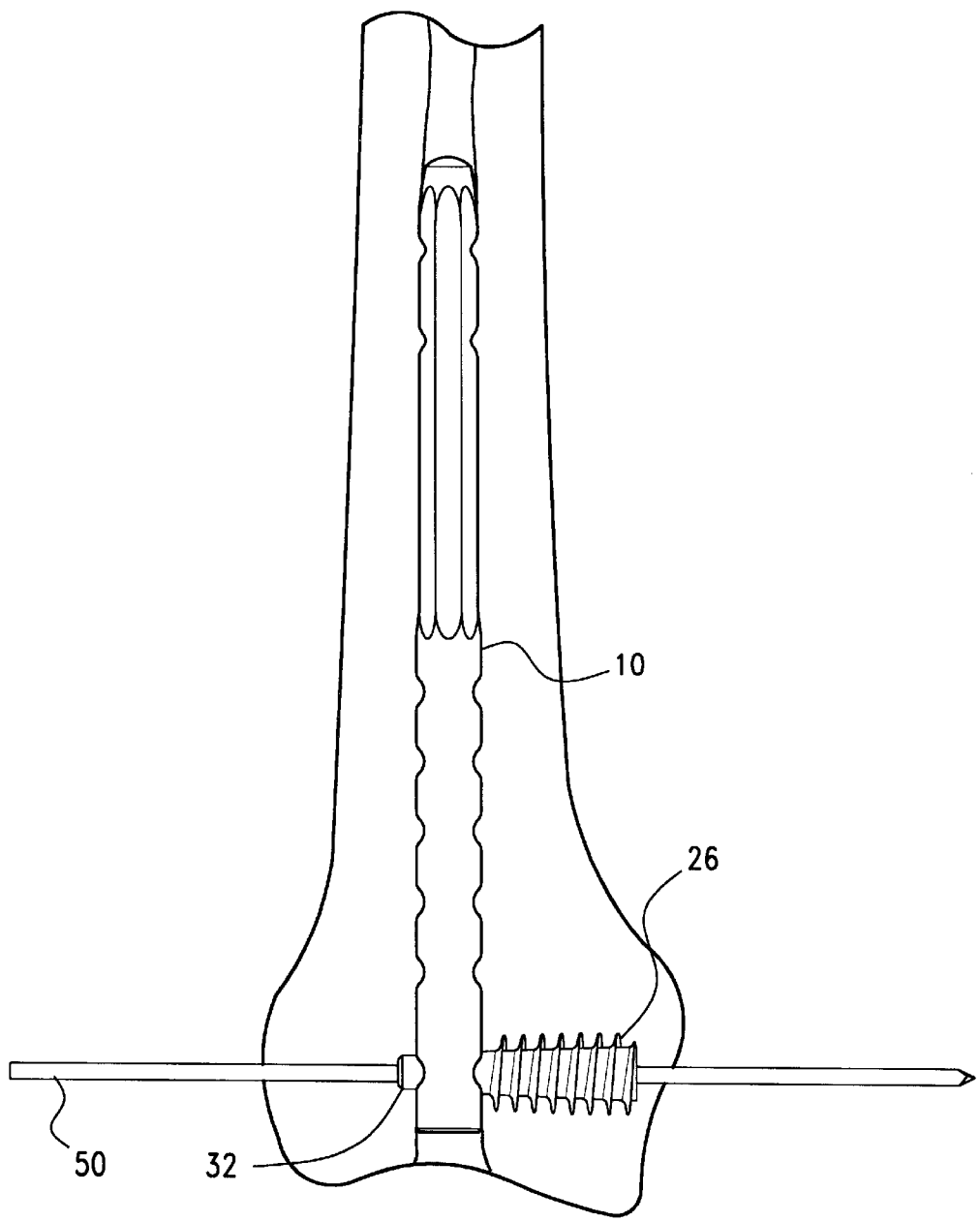
FIG. 11 depicts a step in the embodiment of FIG. 10.

FIG. 11 shows the first lag screw 26 inserted axially along the guide wire 50 into one side of the distal transverse bore 20. Upon insertion into the nail 10, the cylindrical portion 32 of the first lag screw 26 extends through the distal transverse bore 20.

Figure 12:
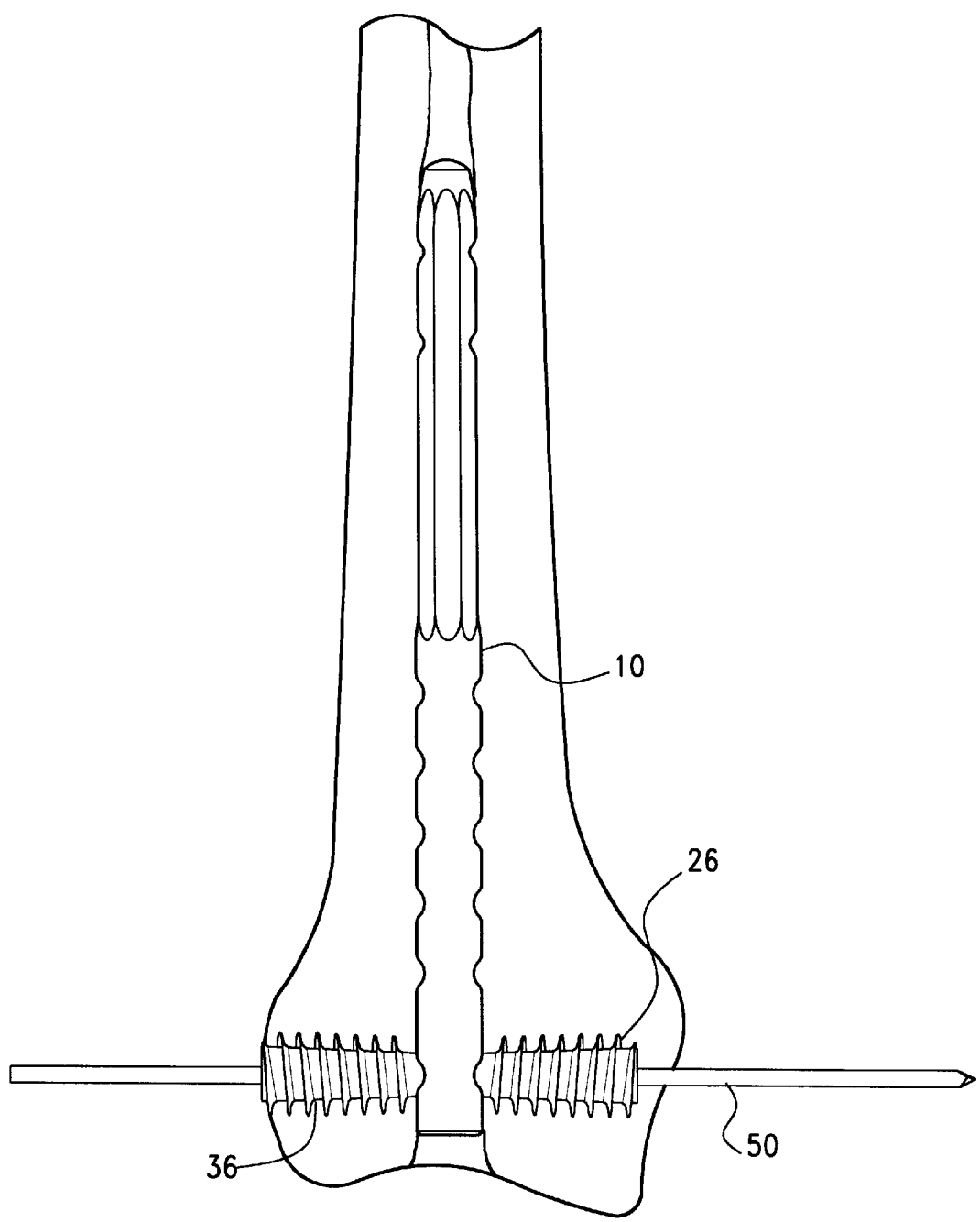
FIG. 12 depicts a next step in the embodiment of FIG. 11.

FIG. 12 shows the second lag screw 36 inserted axially along the guide wire 50 on another side of the distal transverse bore 20. The second lag screw 36 receives and engages the cylindrical portion 32 (not shown) of the first lag screw 26.

Figure 13:
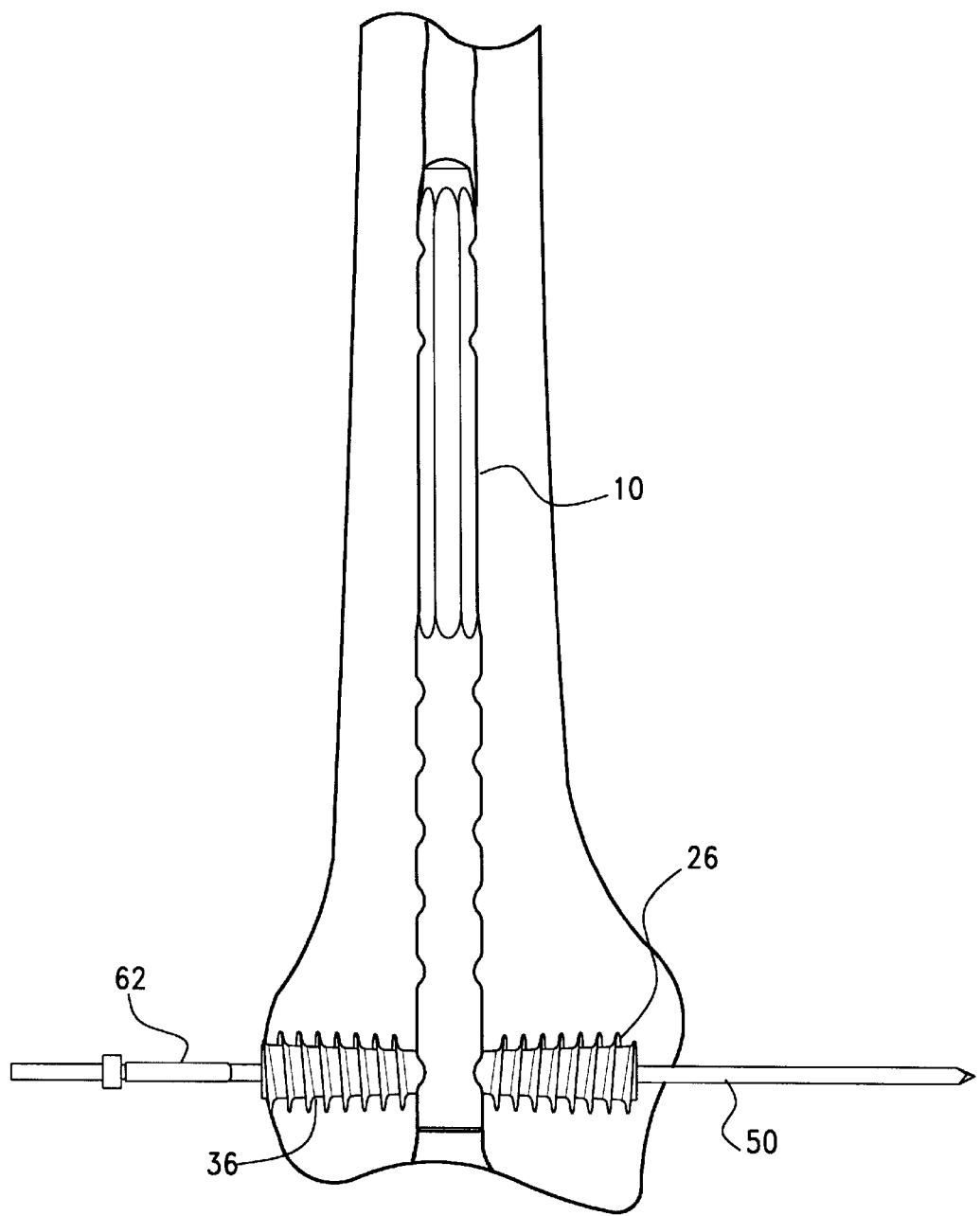
FIG. 13 depicts a next step in the embodiment of FIG. 12.

FIG. 13 shows a locking screw 62 being inserted axially along the guide wire 50.

Figure 14:
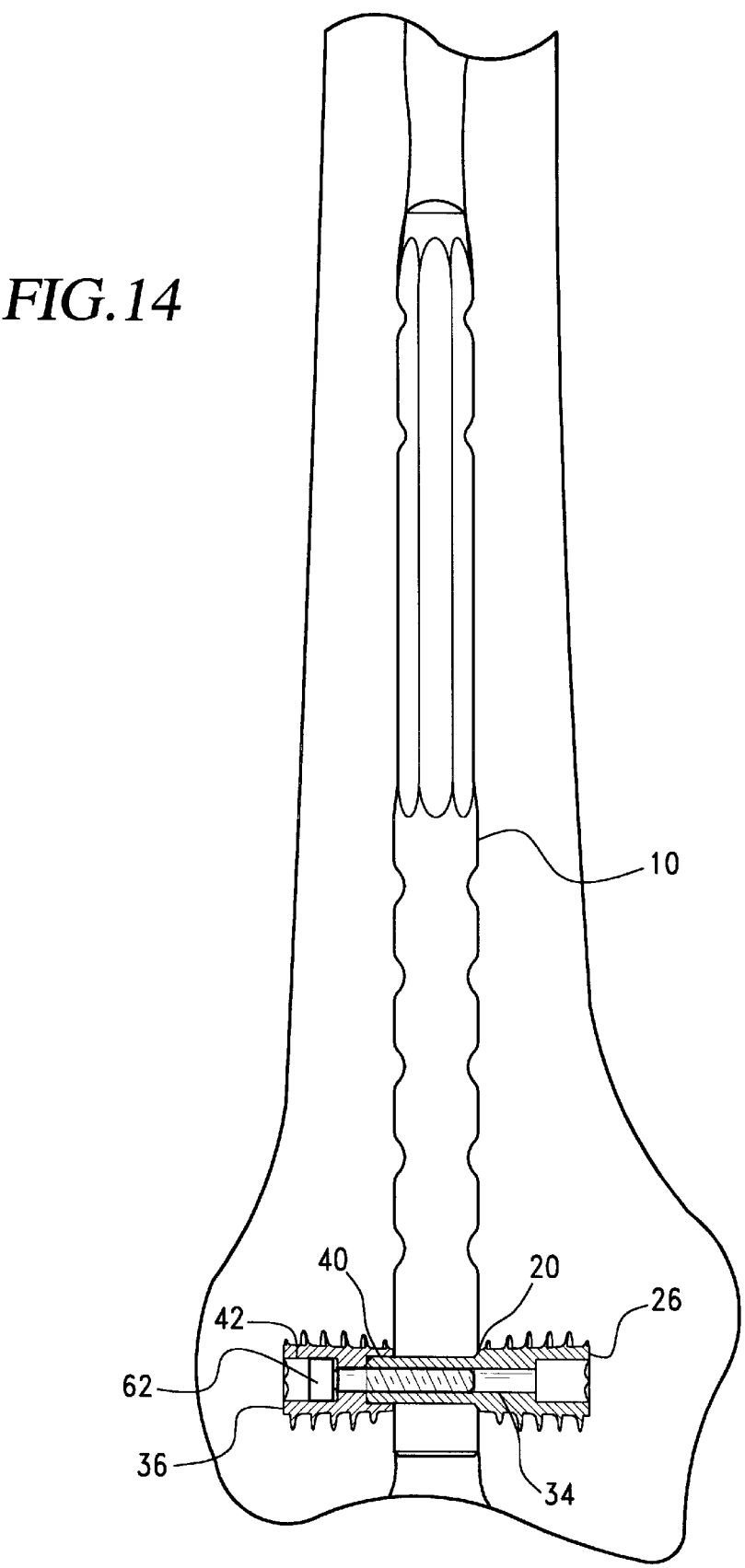
FIG. 14 depicts an assembled, cross-sectional view of an assembled intramedullary nail.

FIG. 14 shows the locking screw 62 as received by the locking screw receiving bore 42 of the second lag screw 36. The locking screw 62 is threaded onto the axial through hole 34 of the first lag screw so as to operatively couple the nail 10, the first lag screw 26 and the second lag screw 36.

Typically, the nails may be manufactured in varying lengths from a biologically inert material which is sterilizable and has the appropriate mechanical strength and stiffness. It will be understood that any or all of the elements constituting the present invention may be included in a kit provided to a medical practitioner. Still further advantages of the present invention should be readily apparent to those of skill in the art based upon the written description provided above.

It should be noted that the invention is not limited for use in the condylar and supracondylar regions of the femur. The intramedullary nail and the interlocking screws can be adapted to stabilize fractures of other bones throughout the human body.

Although multiple preferred embodiments of the invention have been described above, it is to be understood that various modifications could be made to the embodiments by any person skilled in the art without departing from the scope of the invention as defined in the claims that follow, and that the various embodiments could be used interchangeably with other embodiments.

We claim:

1. An intramedullary nail and interlocking screw assembly comprising: a nail having a longitudinal axis and an elongated shank with a distal portion having a distal end and a proximal portion having a proximal end, said distal portion having at least one distal transverse bore located near the distal end, said nail being configured to be inserted from an end of a bone;

an elongate first lag screw having a first outer threaded portion at a first end, a first outer cylindrical portion dimensioned to fit closely within said transverse bore at a second end, and a first axial bore having a first inner threaded portion, said first outer cylindrical and first outer threaded portions being axially spaced along the first lag screw length;

a second lag screw having opposed first and second opposed ends, a second outer threaded portion, a second axial through bore spanning said first and second ends and having a screw seat at a first end and a mating portion adapted to cooperate with the first cylindrical portion of said first lag screw at said second end, said screw seat and said mating portion being axially spaced along the second lag screw length; and an elongate locking screw adapted to fit within said first and second bores, and arranged to engage said first threaded portion and said screw seat to connect said first and second lag screws together within said transverse bore when said first cylinder portion is inserted in said transverse bore, said mating portion is assembled in cooperative relationship with said first cylindrical portion and said locking screw is threaded into said first axial bore and seated on said screw seat.

2. The intramedullary nail and interlocking screw assembly according to claim 1 wherein said outer threaded portions of said first lag screw and said second lag screw each include a minor diameter at the roots of the threads, wherein said minor diameter of said first lag screw progressively decreases from said from said first end of said first lag screw to an end of said first outer threaded portion adjacent to said cylindrical portion, and said minor diameter of said second lag screw progressively decreases from said first end to said second end of said second lag screw.

3. The intramedullary nail and interlocking screw assembly according to claim 1 wherein said first and second outer threaded portion each include a major external thread portion having a taper along the length of said screws wherein said major external thread portion of said first lag screw progressively decreases from said first end of said first lag screw to an end of said first outer threaded portion adjacent to said cylindrical portion and said major external thread portion of said second lag screw progressively decreases from said first end to said second end of said second lag screw.

4. The intramedullary nail and interlocking screw assembly according to claim 3 wherein said outer threaded portions of said first lag screw and said second lag screw each include a minor diameter at the roots of the threads wherein said minor diameter of said first lag screw progressively decreases from said first end of said first lag screw to the end adjacent to said cylindrical portion, and said minor diameter of said second lag screw progressively decreases from said first end to said second end of said second lag screw.

5. The intramedullary nail and interlocking assembly according to claim 1 wherein at least one transverse distal bore extends at an angle with respect to said longitudinal axis of said nail.

6. The intramedullary nail and interlocking assembly according to claim 1 wherein said locking screw includes an axial through hole.

7. The intramedullary nail and interlocking assembly according to claim 1 wherein said first axial bore extends through said first lag screw.

8. The intramedullary nail and interlocking assembly according to claim 1 wherein said second lag screw defining a recess at said first end, said recess axially extending a predetermined distance into said second lag screw, and wherein said screw seat is located at the inner terminus of said recess.

9. A method for interlocking an intramedullary nail implantable within a medullary canal of a bone for stabilizing a fracture, the method comprising the steps of:

providing an intramedullary nail including an elongated shank with a distal portion having a distal end and at least one distal transverse bore;

surgically implanting the intramedullary nail longitudinally into the medullary canal of the bone;

drilling a pilot through hole through a medial lateral direction of the bone along the axis of a distal transverse bore of said nail;

inserting an elongate first lag screw into a first side of said pilot hole, said first lag screw having a first outer cylindrical portion, a first outer threaded portion and a first axial bore having a first inner threaded portion, said outer cylindrical portion extending through and fitting closely within said transverse bore from a first side thereof, said first outer cylindrical and first outer threaded portions being axially spaced along the first lag screw length; and inserting a second lag screw into a second side of said pilot hole, said second lag screw having a second outer threaded portion and an axial through bore having a screw seat, a mating portion and a second inner threaded portion, said mating portion engaging with said outer cylindrical portion of said first lag screw from a side of the transverse bore opposite from said first side, said screw seat and said mating portion axially spaced along the second lag screw length.

10. The method according to claim 9 further comprising the step of inserting a locking screw into said second lag screw, wherein said locking screw threadably engages said first inner threaded portion and said screw seat to connect said first and second lag screws together within said transverse bore so that said mating portion is assembled in cooperative relationship with said first cylindrical portion, whereby said locking screw operatively couples said first and second lag screws with said intramedullary nail.

11. The method according to claim 9 including using a guide wire to guide said first lag screw, said second lag screw and said locking screw, and providing in said first lag screw, said second lag screw and said locking screw an axial through hole for receiving said guide wire.

* * * * *